United States Patent [19]

Schudok et al.

[11] Patent Number: 5,387,514
[45] Date of Patent: Feb. 7, 1995

[54] ACYLATION OF ALCOHOLS WITH *PSEUDOMONAS LIPASE* IMMOBILIZED ON A POLYSTYRENE RESIN

[75] Inventors: Manfred Schudok; Gerd Fülling, both of Frankfurt am Main; Gerhard Kretzschmar, Eschborn, all of Germany

[73] Assignee: Hoechst Aktiengesellschaft, Frankfurt am Main, Germany

[21] Appl. No.: 173,938

[22] Filed: Dec. 28, 1993

Related U.S. Application Data

[63] Continuation of Ser. No. 806,310, Dec. 13, 1991, abandoned.

[30] Foreign Application Priority Data

Dec. 24, 1990 [DE] Germany ............................. 4041777

[51] Int. Cl.⁶ .................. C12P 7/62; C12P 7/02; C12N 11/08; C12N 9/20
[52] U.S. Cl. .................. 435/135; 435/134; 435/155; 435/180; 435/198; 435/874
[58] Field of Search ............... 435/134, 135, 155, 180, 435/198, 874

[56] References Cited

U.S. PATENT DOCUMENTS 4,061,767 12/1977 Ertel et al. ........................ 424/282
4,963,492 10/1990 Keller et al. ..................... 435/155 X

FOREIGN PATENT DOCUMENTS 0322213 6/1989 European Pat. Off. .

*Primary Examiner*—David M. Naff
*Attorney, Agent, or Firm*—Finnegan, Henderson, Farabow, Garrett & Dunner

[57] ABSTRACT

The O-acylation of alcohols is carried out by reacting a vinyl ester or a carboxylic ester with Pseudomonas lipase immobilized on a hydrophobic carrier such as a polystyrene-based carrier. The polystyrene carrier preferably has a surface area of 100–1000 m²/g, a pore volume of 25 to 75% and a pore diameter of 25–1200 Å. Crosslinking may be carried out after the lipase is immobilized on the carrier.

6 Claims, No Drawings

ACYLATION OF ALCOHOLS WITH *PSEUDOMONAS LIPASE* IMMOBILIZED ON A POLYSTYRENE RESIN

This application is a continuation, of application Ser. No. 07/806,310 filed Dec. 13, 1991, now abandoned.

Optically active alcohols are often important chiral precursors of biologically active substances such as, for example, of pharmaceuticals, natural products, crop protection agents or else of liquid crystal components.

An economic preparation process which ensures enzymatic racemate resolution and thus the preparation of the optically active alcohols is therefore of great importance. The same applies to enzymatic stereodifferentiation of prochiral compounds such as, for example, the esterification of enantiotopic hydroxyl groups of 2-substituted 1,3-propanediols. In addition, acylation with enzymatic catalysis is of importance, in contrast to chemical acylation, for particularly sensitive substrates such as, for example, certain primary or secondary alcohols.

Some pharmacological agents whose preparation is facilitated and made more economical by the process according to the invention are products such as NSAIDs (nonsteroidal antiinflammatory drugs), beta-blockers, bronchospasmolytics, antimycotics, pyrethroids, tetramisole, tetrahydrozoline, (R)-(—)-tomoxetine and (S)-(+)-fluoxetine, and prostaglandins and carbohydrates. Chiral building blocks for the synthesis of protease inhibitors, for example of renin, can be obtained considerably more straightforwardly by using enzymatic processes.

It is already known that vinyl esters can be transesterified with enzymatic catalysis and with the addition of alcohols in the presence of solvents such as, for example, tetrahydrofuran (M. Degueil-Castaing et al., Tetrahedron Letters, Vol. 28, No. 9, pages 953-954, 1987). Pig pancreatic lipase was used as enzyme. No stereoselectivity was observed.

Also known is the enzymatic separation of racemic alcohols based on a selective enzyme-catalyzed transesterification reaction with vinyl esters in the absence of solvents. The enzymes used are immobilized lipases from pig liver and pancreas and from the microorganisms Pseudomonas, Candida, Mucor, Rhizopus and Penicillium (EP 032 19 18).

It is furthermore known that it is possible to employ carboxylic esters for the transesterification (G. Carpani, F. Orsini, M. Sisti, L. Verotta, Gazz. Chim. Ital. 119, p. 463-465 (1989)) and cyclic carboxylic anhydrides for the acylation (Y. Terao et al., Chem. Pharm. Bull. 37, p. 1653-1655 (1989)).

In European Patent Application EP 0 25 42 43, chiral compounds are prepared optically pure from prochiral diols by reaction with vinyl acetate in the presence of hydrolases. This is achieved by selective esterification of only one of the two enantiotopic primary OH groups.

It is also known that immobilized lipases can be employed for the hydrolysis and transesterification of fats, oils and similar compounds (M. Mittelbach, J. Am. Oil. Chem. Soc. 67, 168-170 (1990)).

Hsu et al. (Tetrahedron Letters, Vol. 31, No. 44, p. 6403-6406 (1990)) describe the reaction of secondary alcohols using XAD-8 immobilized lipase from Pseudomonas and find an increased rate of reaction of the substrate. However, there are no statements in the publication about the useful lives (stability) or the thermal stability of the immobilized enzyme with negligible loss of activity.

It has now been found, surprisingly, that the O-acylation of alcohols using immobilized Pseudomonas lipase can be carried out particularly efficiently by immobilizing the enzyme by binding to hydrophobic carriers such as polystyrene-based adsorber resins.

Hence the invention relates to:

A process for the acylation of alcohols, where a vinyl ester of the formula I

in which

R$^1$ is hydrogen, $C_1$-$C_{18}$-alkyl which is optionally substituted by halogen, or is phenyl or ($C_1$-$C_3$)-alkoxy-($C_1$-$C_4$)-alkyl and R$^2$ is hydrogen or methyl, or a carboxylic ester of the formula II

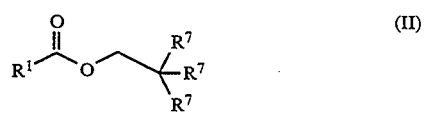

in which R$^1$ has the abovementioned meaning, and R$^7$ is either fluorine, chlorine or hydrogen, where all R$^7$ must be identical, or R$^7$ is fluorine, chlorine, bromine or cyano and hydrogen, where two R$^7$ must be hydrogen, or R$^7$ is fluorine or chlorine and hydrogen, where only one R$^7$ is hydrogen and the two other substituents are identical, or one of the cyclic carboxylic anhydrides succinic or glutaric anhydride is reacted with an alcohol in the presence of immobilized Pseudomonas lipase, which comprises employing Pseudomonas lipases which are immobilized on polystyrene-based adsorber resins.

The invention is described in detail hereinafter, especially in its preferred embodiments. The invention is furthermore defined by the contents of the claims.

In the process according to the invention, the vinyl or methylvinyl ester or the carboxylic ester of the formula II or the cyclic carboxylic anhydride, which acts as solvent or is dissolved in another organic solvent, is cleaved into a ketone, aldehyde or alcohol and an acyl radical, the latter undergoing enzymatic acylation with the added alcohol (substrate).

Suitable carrier materials are polystyrene-based adsorber resins. All carriers can be obtained commercially.

The polystyrene-based carrier materials which are used have a pore volume of 25-70, but preferably 35-55%, a surface area of 100-1000 m$^2$/g, but preferably 200-750 m$^2$/g, and a pore diameter of 25-1300 Å, preferably 50-250 Å.

Employed as enzyme are Pseudomonas lipases [lipase P from Pseudomonas cepacia (also called FP or PS) Amano Pharmaceuticals, Nagoya, Japan].

To immobilize the enzyme, 0.01 to 2 g, but preferably 0.1-1.5 g, of enzyme per 10 ml of carrier are stirred in 0,005-1M potassiumphosphate buffer, pH 5-9, but preferably pH 6-8, for 1-20 h. After the reaction time, the buffer is removed by filtration with suction through a frit, and the enzyme/carrier mixture is washed with large quantities of water, acetone and vinyl acetate. The carrier is ready for use in this state and can be stored in the dry state.

The quantity of carrier to be loaded with enzyme is chosen freely depending on the size of the batch, on the reactivity of the alcohol, on the expected reaction time and on the required level of conversion. It can easily be determined by preliminary tests.

The vinyl and methylvinyl esters of the formula I which cannot be bought can be prepared in a straightforward manner, for example by noble metal-catalyzed transesterification of vinyl acetate with the appropriate carboxylic acids. The transesterification is preferably catalyzed by $Pd^{2+}$.

The vinyl esters can also be synthesized by an $Hg^{2+}$-catalyzed addition of acetylene.

The carboxylic esters of the formula II, just like the cyclic carboxylic anhydrides (succinic and glutaric anhydride), can be bought or prepared by standard processes.

The alcohols which cannot be bought are obtained, for example, by reduction of the corresponding ketones, most of which can be bought, or by a-halogenation of corresponding ketones with subsequent reduction to the alcohol. Other alcohols or ketones which cannot be bought can be prepared straightforwardly by processes known from the literature, for example by Grignard or other conventional addition reactions.

By alcohols are meant an alcohol of the formula III

in which
$R^3$ is $C_1$–$C_{18}$-alkyl or $C_3$–$C_{10}$-cycloalkyl, it also being possible for these radicals to be halogen-substituted, and
$R^4$ is epoxy-$C_1$–$C_5$-alkyl, where the epoxy group is in the position β to the OH group in the radical of the formula II or
$R^4$ is $C_1$–$C_{10}$-alkyl, $C_2$–$C_{10}$-alkenyl, $C_2$–$C_{10}$-alkynyl, $C_3$–$C_8$-cycloalkenyl, where the alkyl, alkenyl, alkynyl and cycloalkenyl radicals are optionally substituted by COOH, halogen, $NO_2$, CN, $C_1$–$C_4$-alkoxycarbonyl or phenyl, it being possible in turn for the phenyl radical to be substituted by halogen, $NO_2$, CN or $C_1$–$C_4$-alkoxy, or $R^4$ is aryl or heteroaryl, where the aryl or heteroaryl radicals are optionally substituted by $C_1$–$C_4$-alkyl, $C_1$–$C_4$-alkoxy, halogen, $NO_2$, CN or N-PG, where PG is an amino-protective group,
or in which
$R^3$ and $R^4$ together are an alkylene or alkenylene radical of the formula IVa, b

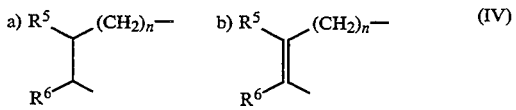

in which
n is 1, 2 or 3, and
$R^5$ and $R^6$ are identical or different and are hydrogen, $C_2$–$C_4$-alkenyl, or $C_1$–$C_4$-alkyl or
$R^5$ and $R^6$ together are fused-on phenyl or fused-on naphthyl, where the phenyl or naphthyl radical is optionally substituted by $C_1$–$C_4$-alkyl, $C_1$–$C_4$-alkoxy, $NO_2$, CN or halogen, it also being possible for a methylene unit in the alkenylene chain to be replaced by a carbonyl group, or
an alcohol of the formula V

in which
$R^8$ is hydrogen or an alkyl group and
$R^9$ is alkyl, aralkyl, aryl, benzyl or a naphthylmethyl group.

It is also possible to use all polyhydric alcohols as substrate.

By halogens in the alcohol of the formula III are meant fluorine, chlorine, bromine and iodine, especially chlorine and bromine. By "aryl" are meant, for example, phenyl, naphthyl, phenanthryl, anthryl and fluorenyl, especially phenyl, naphthyl and phenanthryl. By "heteroaryl" are meant, for example, furyl, thienyl, pyrrolyl, pyridyl, pyrimidyl, pyrazinyl, pyridazinyl, pyrazolyl, isoxazolyl, imidazolyl, oxazolyl, thiazolyl and indolyl, especially furyl, thienyl, pyrrolyl and pyridyl. By the amino-protective group "PG" are meant the amino-protective groups customarily employed in peptide chemistry, for example benzyloxycarbonyl (Z), benzoyl, benzyl, butyloxycarbonyl (Boc), 9-fluorenylmethoxycarbonyl (Fmoc), benzhydryl, allyloxycarbonyl (Aloc), tosyl, methoxymethyl (MOM), tetrahydropyranyl (THP), acetyl, but also alkyl or cycloalkyl groups, such as for example, N-methyl, N,N-dimethyl. By "fused-on phenyl" or "fused-on naphthyl" is meant a phenyl or naphthyl radical in which the C—C double bond of the radical of the formula III is part of the phenyl or naphthyl radical. The optionally substituted radicals $R^1$, $R^3$, $R^4$, $R^5$ and $R^6$ are preferably monosubstituted.

Alkyl and alkenyl radicals with 3 and more carbon atoms, and alkynyl radicals with 4 and more carbon atoms, can be both straight-chain and branched.

The alcohol to be acylated is employed in a concentration of 0.05–200%, preferably 0.5–10%, based on the volume of the vinyl ester.

At least 0.5 mole equivalents of the vinyl radical must be employed for the acylation of the alcohol.

The reaction of the alcohols is carried out batchwise or in a continuous process.

The racemate resolution of the alcohols can be carried out in the process according to the invention with an increase in activity of at least 90% compared with conventional processes.

The enzyme immobilized on a carrier shows scarcely any loss of activity in the continuous process even after some months of use, in which there is alternation of reaction runs and phases of non-use of the immobilized enzyme. This even applies when the reaction is carried out at elevated temperatures.

For batchwise reaction with immobilized Pseudomonas lipase, the vinyl ester of the formula I or the carboxylic ester of the formula II or the cyclic carboxylic anhydride, but preferably vinyl acetate or a solution of the vinyl ester, is introduced into a (non-polar) organic solvent, and the alcohol to be reacted is added. Suitable and preferred solvents are ethers, but very particularly symmetrical and unsymmetrical, branched and unbranched dialkyl ethers. Also suitable and preferred are hydrocarbons, very particularly linear, branched or cyclic hydrocarbons of $C_4$-$C_8$. Pseudomonas lipase immobilized on a carrier is added to the suspension, and is stirred or shaken at constant temperature. The completion of the reaction is checked by TLC, GC or HPLC. The immobilized enzyme is subsequently removed by filtration and thoroughly washed with a solvent (see above) or vinyl acetate, and the solution is concentrated in vacuo. The alcohol/ester mixture which remains as residue in the case of racemate resolution is separated by column chromatography on silica gel or by extraction, crystallization or distillation. Other acylation products frequently result in sufficient purity so that purification is unnecessary.

To carry out the reaction in the continuous process, the Pseudomonas lipase P/FP/PS which is immobilized on a carrier is packed into a glass column and washed with the solvent in which the reaction is carried out, i.e. with vinyl acetate, another vinyl ester or another organic solvent.

The substrate solution is subsequently allowed to run through at a constant rate at constant temperature.

The ratio of carrier [ml] to immobilized lipase [g] to vinyl acetate [ml] to the concentration of the substrate [% by volume] is in the range 5-100:1:5-10,000:0.5-200 when vinyl acetate is employed (i.e. without further addition of solvent).

If the reaction is carried out in a vinyl ester, the alcohol to be acylated is employed in concentrations of 0.05-200% by volume.

The level of the conversion can be controlled virtually as required by adjusting the dropping rate and can easily be determined by preliminary tests.

The space-time yields depend directly on the absolute values of the abovementioned parameters, but especially on the column dimensions, i.e. the quantity of enzyme which is immobilized on the carrier in the column.

The column dimensions can be chosen freely but, on the laboratory scale, are preferably of the order of 10-500 ml. With a preferred column packing with 50 ml of enzyme immobilized on a carrier, with a 1% strength substrate solution and with a flow rate of 10 drops/min, space-time yields of about 0.5-300 g/l/h are achieved.

The reaction temperature during the process is $(-)10°$ to $(+)100°$ C., preferably $(+)0°-60°$ C.

The reaction times depend on the nature of the alcohol to be reacted, the concentration thereof and the quantity of the enzyme immobilized on the carrier and vary between 1 h and 4 weeks. They are preferably between 3 h and 3 days.

The products acetaldehyde or acetone resulting from the process according to the invention, and the alcohols liberated for the acylation, as well as the enantiomeric alcohols (substrates) resulting in the case of selective acylation, i.e. carboxylic esters and unreacted alcohol, can be separated in a known manner by using all customary methods, which have, however, to be tested in the individual case, preferably by chromatography on silica gel or one of the other abovementioned processes.

EXAMPLE

General procedure

To immobilize the enzyme, the carrier material is either
a) employed untreated,
b) subsequently crosslinked with glutaraldehyde after the enzyme immobilization (Tab. 1)

re a) To immobilize the lipase on the carrier, 50 ml of the carrier are suspended in 100 ml of potassium phosphate buffer, pH 7.0, and 500 mg of lipase P are added. The mixture is stirred at RT for 3 h, filtered and washed thoroughly with water.

re b) Subsequent crosslinking For the subsequent crosslinking, the process is carried out as described in a) but, after the stated immobilization time, crosslinking is carried out with 4 ml of glutaraldehyde solution (25% strength). After 1 hour, the enzyme immobilized on the carrier is filtered off and washed with water.

The preferred carriers may be characterized as follows:

|  | ®XAD-2 | ®XAD-4 |
| --- | --- | --- |
| Pore volume [%] | 42 | 51 |
| Density | 1.02 | 1.02 |
| Surface area [m$^2$/g] | 330 | 750 |
| Pore diameter [Å] | 90 | 50 |

The carrier is stored in water or dry.

500 mg of the alcohol to be reacted are suspended in 20 ml of vinyl acetate. To this is added the immobilized lipase, and the mixture is stirred at constant temperature.

After the reaction is complete, the immobilized enzyme is removed by filtration. The remaining solution is completely evaporated in vacuo.

The acylation products present in the residue can be separated by standard processes, for example by silica gel chromatography.

Table 2 indicates the starting materials and resulting products, the variable process parameters (quantity of enzyme, quantity of carrier, quantity of alcohol, quantities of vinyl esters, reaction temperature, reaction time) and the product characteristics and chemical yield.

For accurate determination of the activity it is necessary to determine accurately the quantity of enzyme bound to the carrier.

The basic assumption in the tests described here for the process according to the invention is that Pseudomonas lipase is a single protein with a salt content of 37% or 63% of the protein (% by weight). This salt content is determined by dialysis.

To determine the immobilization yield, the test which has already been described is carried out with a batch of 20 ml of XAD-2 carrier and 2 g of Pseudomonas lipase. The immobilization and washing solutions are collected, combined and lyophilized. 1.77 g of residues composed of enzyme and buffer salts are obtained from this pool. It is known from the weight obtained after lyophilization of pure buffer that the quantity of salt is 0.38 g in the quantity of buffer solution employed.

Thus, from the 1.77 g of residue it is necessary to subtract, on the one hand, 0.38 g of buffer salts and, on the other, 0.74 g of salts of the enzyme (=37%; see above).

The remaining quantity of 0.65 g ought to correspond to the quantity of non-immobilized enzyme.

Subsequent dialysis of the residue shows that a small quantity of salt is still present, so that the quantity of enzyme remaining is 0.58 g instead of the theoretical value of 0.65 g. Thus the quantity of immobilized enzyme is between 0.61 and 0.68 g. This means that the immobilization yield is 51%.

The calculation is carried out once more by way of example for Example 1 (phenylethanol) mentioned in Table 2.

---

50 mg of lipase P (obtained commercially) ×
    0.63 actual content of lipase P enzyme ×
    0.51 immobilization yield →
    16 mg of lipase immobilized on the carrier
50 mg of free lipase P ×
    0.63 actual content of lipase P enzyme →
    31.5 mg of actual content of lipase P enzyme
16 mg of immobilized enzyme provide a conversion of 33.4%
31.5 mg of free enzyme provide a conversion of 20.7% →
    activity: 320%.

---

The enzymatic racemate resolution can be carried out not only as described above in the presence of vinyl acetate but also in the presence of other vinyl esters such as, for example, of chloroacetic acid, lauric acid and phenylacetic acid. For this, lipase P immobilized on the carrier is packed into a glass column and washed with 150 ml of t-butyl methyl ether, which is used as solvent for the following reaction.

The column is subsequently charged with a solution of substrate and vinyl ester, each of which are dissolved in 250 ml of t-butyl methyl ether. This solution is allowed to run slowly through the column, and the composition after the solutions have completely passed through is determined by gas chromatography. The quantities to be employed, and the flow-through and reaction times and the results are to be found in Table 3.

Example of transesterification with ethyl acetate:

0.5 ml of ethyl acetate is stirred with 2.5% strength phenylethanol in t-butyl methyl ether (10 ml) and 5 ml of enzyme immobilized on XAD-2 (theoretical quantity of enzyme: 50 mg) at room temperature. The reaction showed 50% conversion of the phenylethanol after 5 days.

The control with non-immobilized enzyme showed a distinctly lower conversion after 7 days.

The conversion was determined by TLC.

Example of the esterification of primary OH groups:

Geraniol is dissolved 2.5% strength in 10 ml of vinyl acetate and stirred with the addition of 5 ml of enzyme immobilized on XAD-2 (theoretical quantity of enzyme: 50 mg) at room temperature. Quantitative acetylation was carried out with immobilized enzyme after only 1 h, whereas the free enzyme required 50% more time.

Example of the acetylation of dl-pantolactone - test of the long-term stability at elevated temperature in a continuous process:

400 ml of lipase P immobilized on XAD-2 are packed into a temperature-controllable jacketed glass column. A 0.1% strength solution of dl-pantolactone (in vinyl acetate/t-butyl methyl ether 1:9; total volume 2 l) is passed at a flow rate of 0.11 ml/min through the column at 50° C.

The column volume is compensated by subsequent washing with t-butyl methyl ether at the same rate. GC analysis of the reaction solution shows 71.6% conversion to pantolactone acetate in this first run. The washed column is stored in the dry state at RT and temperature-equilibrated for 5 h before each new start of another run. During the next 5 months a further 11 continuous reactions are carried out in this manner. The 12th run (under identical conditions apart from: flow rate 0.13 ml/min), carried out 5 months later, shows 70.7% conversion to pantolactone acetate.

TABLE 1

| | | Previously functionalized with chloro-acetic acid | Subsequently crosslinked with glutaraldehyde | % conversion to acetate | | | | |
|---|---|---|---|---|---|---|---|---|
| Ex. No. | Carrier | | | 1st Run | 2nd | 3rd | 4th | Quantity used |
| | Control | | | 15–17 | 4–6 | | | in each case |
| 1 | ®Amberlite XAD-2 | — | — | 33.4 | 38.4 | 38 | 33.5 | (X) |
| 2 | XAD-4 | — | — | 19.35 | 11.94 | 12.31 | 8.08 | |
| | XAD-16 | — | — | 17.20 | 14.11 | 14.91 | 10.06 | |
| | XAD-1180 | — | — | 17.61 | 13.03 | 12.71 | 11.19 | |
| 3 | XAD-12 | — | — | 19 | 4.45 | — | — | |
| 4 | XAD-2 | — | yes | 18.45 | 24.93 | 17.31 | 13.46 | |
| 5 | XAD-4 | — | yes | 15.66 | 16.74 | 14.63 | 11.91 | |
| 6 | XAD-12 | — | yes | 26.06 | 9.7 | — | — | |

(X) The following were used in Example 1: 250 mg of phenylethanol, 10 ml of vinyl acetate, 5 ml of carrier.

TABLE 2

(Amberlite XAD-2 was used as carrier in each case)

| | | | | Quantity | | | Quantity | | |
|---|---|---|---|---|---|---|---|---|---|
| | Racemo: | Precursor | | A: | B: | | of vinyl | Reaction | Conver- |
| Ex. No. | prochir. alcohol | Quantity [g] | Conc. in % | carrier [ml] | enzyme [g] | Temp. [°C.] | ester [ml] | time [h] | sion [%] |
| 1 | 1-phenyl-ethanol | A: 0.25 | 2.5 | 5 | 0.05 | RT | 10 | 6 | 33.4 |
| | | B: 0.25 | 2.5 | | 0.05 | RT | 10 | 6 | 20.7 |
| | | C: 0.5 | 1 | 50 | 5 | RT | 50 | — | 50 |
| 2 | 1-phenyl-propanol | A: 0.50 | 2.5 | 10 | 1 | RT | 20 | 30 | 46.1 |
| | | B: 0.52 | 2.5 | | 1 | RT | 20 | 30 | 37.1 |
| | | C: — | — | — | — | RT | — | — | — |
| 3 | 2-chloro-1-phenyl-ethanol | A: 0.51 | 2.5 | 10 | 1 | RT | 20 | 48 | 51.7 |
| | | B: 0.51 | 2.5 | | 1 | RT | 20 | 48 | 32.3 |
| | | C: 0.5 | 0.2 | 50 | 5 | RT | 50 | — | 34 |
| 4 | panto-lactone | A: 0.5 | 2.5 | 10 | 1 | RT | 20 | 48 | 32.2 |
| | | B: 0.49 | 2.5 | | 1 | RT | 20 | 48 | 29.7 |
| | | C: 0.5 | 0.2 | 50 | 5 | 50° C. | 250 | — | 42 |

TABLE 2-continued (Amberlite XAD-2 was used as carrier in each case)

| | | | | | | | | | |
|---|---|---|---|---|---|---|---|---|---|
| 5 | alleth-rolone | A: 0.5 | 2.5 | 10 | 1 | RT | 20 | 4 | 45 |
| | | B: 0.51 | 2.5 | | 1 | RT | 20 | 4 | 42 |
| | | C: 0.5 | 1 | 50 | 5 | RT | 500 | — | 64 |
| 6 | 1-(6-acetoxy-naphthyl)-ethanol | A: — | — | — | — | — | — | — | — |
| | | B: — | — | — | — | — | — | — | — |
| | | C: 14 | 1 | 50 | 5 | RT | 1400 | — | 52 |
| 7 | 2-(1-naphthyl-methyl)-propane-1,3-diol | A: 1 | 2 | 2.5 | 0.25 | 0° C. | 50* | 16 | 98 |
| | | B: 1 | 2 | | 0.25 | 0° C. | 50* | 16 | 95 |
| | | C: 1 | 0.5 | 50 | 5 | 15° C. | 200* | 6 | n.d. |

| Ex. No. | Racemo: prochir. alcohol | Act. [%] | Space-time yield [g/l/h] | ee | Alcohol $[\alpha]_D^{25}$ | chem. yield | ee | Acetate $[\alpha]_D^{25}$ | chem. yield |
|---|---|---|---|---|---|---|---|---|---|
| 1 | 1-phenyl-ethanol | 320 | — | n.d. | n.d. | n.d. | >95% | +105.6 | n.d. |
| | | — | — | " | " | " | >95% | +105.1 | n.d. |
| | | — | 3 | >95% | −44 | 43% | >95% | 104.1 | 44% |
| 2 | 1-phenyl-propanol | 250 | — | 77% | −38 | 45% | >95% | 102.7 | 36% |
| | | — | — | 55% | −27.4 | 54% | >95% | +100.1 | 33% |
| | | — | — | — | — | — | — | — | — |
| 3 | 2-chloro-1-phenyl-ethanol | 320 | — | n.d. | n.d. | 35% | >95 | +75.6 | 39% |
| | | — | — | n.d. | n.d. | 62% | >95% | — | 25% |
| | | — | 0.5 | n.d. | n.d. | n.d. | n.d. | n.d. | n.d. |
| 4 | panto-lactone | 220 | — | n.d. | n.d. | 38% | >95% | +12.7 | 22% |
| | | — | — | n.d. | n.d. | 63% | >95% | +12.7 | 28% |
| | | — | 0.5 | n.d. | n.d. | n.d. | >95% | +11.4 | 37% |
| 5 | alleth-rolone | 210 | — | >95% | +14.5 | 42% | >84% | −27.6 | 44% |
| | | — | — | >95% | +14.8 | 43% | 92% | −29.9 | 41% |
| | | — | 6 | >95% | +14.6 | 28% | 52% | −15.87 | 63% |
| 6 | 1-(6-acetoxy-naphthyl)-ethanol | — | — | — | — | — | — | — | — |
| | | — | 3 | >95% | −30 | 45% | 92% | +82.35 | 48% |
| 7 | 2-(1-naphthyl-methyl)-propane-1,3-diol | 190 | — | — | — | — | 95% | +39.5 | 94% |
| | | — | — | — | — | — | 97% | +40.3 | 91% |
| | | — | 30 | — | — | — | 88% | +36.5 | n.d. |

A = batch test with immob. enzyme
B = comparison batch with free enzyme
C = test in continuous process
RT = room temperature
n.d. = not determined
*= a vinyl acetate/dimethoxyethane/diethyl ether mixture was used
ee: measured on the basis of the optical rotation

TABLE 3

Acylation of phenylethanol in various vinyl esters

| Ex. No. | Rac. alcohol+ [g] | Vinyl ester Type/Quantity [ml] | Quantity enzyme/carrier* | Reaction time [h] | Conversion [%] |
|---|---|---|---|---|---|
| 1 | 2.5 g | chloroacetic acid/12.5 | 5/50 | 5 | 67.6 |
| 2 | 2.5 g | lauric acid/5 | 5/50 | 5 | 41.7 |
| 3 | 2.5 g | phenylacetic acid/5 | 5/50 | 16 | 24.4 |

+phenylethanol was employed as rac. alcohol in each case.
* ®Amberlite XAD-2 was employed as carrier in each case.

The process according to the invention has the following advantages compared with conventional processes for racemate resolution of alcohols:

A) The space-time yields are distinctly increased owing to increased enzyme activity.
B) Very long useful lives of the immobilized enzyme permit particularly economic use of the biocatalyst.
C) The activity of the enzyme is durable (Tab. 1; see below (a)).
D) High thermal stability of the immobilized enzyme. 10 ml of 0.5% strength phenylethanol solution in toluene are mixed with 100 mg of free lipase or 1 ml of immobilized enzyme and subsequently with 0.1 ml of vinyl phenylacetate in each case. The free lipase shows 3.2% conversion after stirring at RT for 5 hours, and no longer shows activity after the same time has elapsed under reflux at 110° C., whereas the immobilized lipase still shows 1-2% conversion at 110° C. The conversion is determined by GC test (Reoplex on ®Chromosorb).

(a) 250 mg of racemic phenylethanol in 20 ml of vinyl acetate are shaken with 2 ml of immobilized lipase at 50° C. for 6 h. The conversion is subsequently determined by GC, and the immobilized enzyme is removed by filtration and thoroughly washed with vinyl acetate. Renewed reaction under identical conditions is carried out the next day.

(b) The process is carried out in the same way using 0.2 g of the free enzyme.

(a) A conversion of 48.7% is measured in the 1st run after 6 h.
A conversion of 21.2% is measured in the 10th run after 6 h.

(b) In the 1st run, the conversion after 6 h is 46.1%.
Product no longer detectable after the 7th run.

The activity of the enzyme is ensured in the long term.

We claim:

1. A process for the acylation of alcohols, which comprises reacting a vinyl ester of formula I

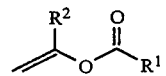

(I)

in which $R^1$ is hydrogen, $C_1$-$C_{18}$-alkyl which is optionally substituted by halogen, or is phenyl or ($C_1$-$C_3$)- alkoxy-($C_1$-$C_4$)alkyl and $R^2$ is hydrogen or methyl, or reacting a carboxylic ester of formula II

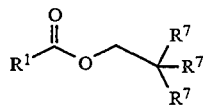 (II)

in which $R^1$ has the above-mentioned meaning, and $R^7$ is either fluorine, chlorine or hydrogen, where all $R^7$ must be identical, or $R^7$ is fluorine, chlorine, bromine or cyano and hydrogen, where two $R^7$ must be hydrogen or is fluorine $R^7$ is fluorine or chlorine and hydrogen, where only one $R^7$ is hydrogen and the two other substituents are identical, or one of a cyclic carboxylic anhydride selected from the group consisting of succinic anhydride and glutaric anhydride with an alcohol in the presence of immobilized Pseudomonas lipase wherein the Pseudomonas lipase is immobilized on a polystyrene-based adsorber resin having a surface area of 100–1000 $m^2$/g, a pore volume of 25 to 75% and a pore diameter of 25–1200 Å.

2. The process as claimed in claim 1, wherein the reaction is carried out batchwise.

3. The process as claimed in claim 1, wherein the reaction is carried out in a continuous process.

4. The process as claimed in claim 1, wherein the polystyrene-based adsorber resin is subsequently crosslinked with glutaraldehyde after coupling of the enzyme.

5. The process as claimed in claim 1, wherein the reaction temperature is $-10°$ to $+100°$ C.

6. The process as claimed in claim 1, wherein the reaction temperature is $0°$ to $+60°$ C.

* * * * *